United States Patent
Tasca

[11] Patent Number: 5,184,071
[45] Date of Patent: Feb. 2, 1993

[54] NON-DESTRUCTIVE EDDY CURRENT TEST DEVICE USING ADDITIVE FLUX SUBSTRACTIVE FLUX SWITCHING

[75] Inventor: Jean-Pierre Tasca, Sainte Genevieve Des Bois, France

[73] Assignee: Compagnie Generale D'Automatisme CGA-HBS, Bretigny-Sur-Orge, France

[21] Appl. No.: 805,962

[22] Filed: Dec. 12, 1991

[30] Foreign Application Priority Data

Dec. 28, 1990 [FR] France ................. 90 16469

[51] Int. Cl.⁵ .............. G01N 27/90; G01R 33/12
[52] U.S. Cl. .................... 324/238; 324/232; 324/233
[58] Field of Search ............. 324/227, 232, 233, 234, 324/237, 238

[56] References Cited

U.S. PATENT DOCUMENTS 3,609,531  9/1971  Forster ..................... 324/227
3,701,941 10/1972  Bantz et al. ............... 324/238
3,866,116  2/1975  Strauts et al. ............. 324/228
5,068,608 11/1991  Clark, Jr. ................. 324/232 X

FOREIGN PATENT DOCUMENTS 2035571  6/1980  United Kingdom .

Primary Examiner—Gerard R. Strecker
Attorney, Agent, or Firm—Sughrue, Mion, Zinn, Macpeak & Seas

[57] ABSTRACT

A non-destructive eddy current test device using additive flux/substractive flux switching includes a generator supplying a sinusoidal signal, two power amplifiers of equal and opposite gain, a changeover relay, two impedances and two coils forming a Wheatstone bridge, an amplifier controlled by a binary signal to add or subtract and two synchronous detectors for supplying signals representing the real part and the imaginary part of the difference between the complex impedances of the coils. A control device supplies to the changeover relay and to the amplifier a control signal for obtaining additive or subtractive fluxes in the two coils and for respectively subtracting or adding the two output voltages of the Wheatstone bridge. The device is applicable to the non-destructive testing of metal parts.

3 Claims, 2 Drawing Sheets 5,184,071

NON-DESTRUCTIVE EDDY CURRENT TEST DEVICE USING ADDITIVE FLUX SUBSTRACTIVE FLUX SWITCHING

BACKGROUND OF THE INVENTION

1. Field of the invention

The invention concerns a non-destructive eddy current test device using additive flux/subtractive flux switching.

2. Description of the prior art

A device of this kind is used, for example, to detect defects or foreign bodies or variations of composition in a metal part. It uses a method based on generating eddy currents at a point in the part under test, subjecting this point to an alternating magnetic field and detecting variations of the eddy currents relative to a reference by detecting variations in the impedance of at least one coil used to generate the eddy currents.

The method is usually a differential method entailing generating eddy currents at two adjacent points in the same part using two identical coils carrying the same current either in phase or 180° out of phase and measuring the difference between the impedances of the two coils. There is no difference if the two points on the part under test have the same composition, even if the temperature is different, and no previous calibration is required. There is a difference if the composition of the part is not exactly the same at the two points at which the coils are located.

As the two coils are located at adjacent points, their magnetic fluxes add or subtract according to the direction of the current in each of the two coils and the direction in which each of the two coils is wound. The two coils constitute a probe which may be remote from the remainder of the test device. Each coil is connected to the remainder of the test device by a coaxial cable which can be up to 200 meters longs. Experience shows that it is sometimes possible to obtain greater resolution by unplugging and interchanging the two terminals of one coil to reverse its flux.

This method of additive flux/subtractive flux switching is not very practical and may even be virtually impossible to use if the coils are very far from the remainder of the test device and are virtually inaccessible. An aim of the invention is to remedy this drawback of prior art devices.

SUMMARY OF THE INVENTION

The invention consists in a non-destructive eddy current test device using additive flux/subtractive flux switching comprising:

means for supplying first and second alternating currents at the same frequency;
two analogous coils respectively carrying the first and the second current, said two coils being adjacent each other and each being electromagnetically coupled to a part under test so as to create therein two fluxes which are either added or subtracted according to the directions of the two currents and according to the directions in which the two coils are wound;
means for measuring the difference between the impedances of the two coils; and
wherein to enable additive flux/subtractive flux switching said means for supplying the first and second current comprise:
means for supplying a first excitation signal;
means for supplying a second excitation signal in phase opposition to said first excitation signal;
means for feeding said first excitation signal to one coil and for feeding to the other coil either the first or the second excitation signal as determined by control means;
and wherein said means for measuring the impedance difference comprise means for obtaining either the sum or the difference of the two voltages at the terminals of the two coils as determined by said control means.

This device provides additive flux/subtractive flux switching without manual operation at the probe comprising the two coils because the flux in one of the coils is reversed by means which may be sited remotely of the two coils.

The invention will be better understood and other features of the invention will emerge from the following description and the appended drawings.

DETAILED DESCRIPTION OF THE INVENTION

Figure 1:
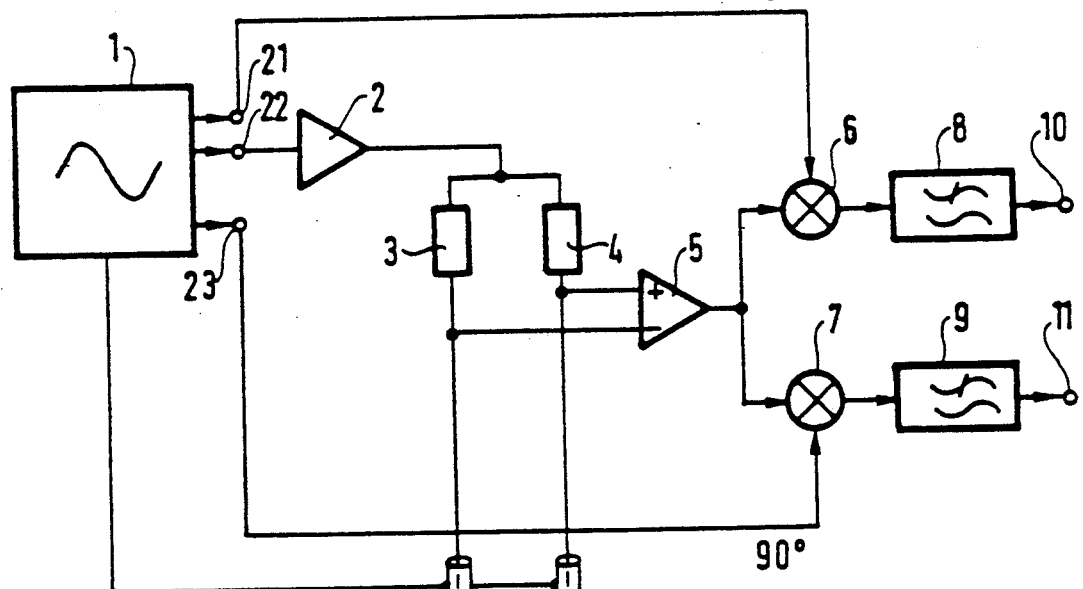
FIG. 1 is a block diagram of one embodiment of prior art non-destructive eddy current test device.

The prior art device shown in FIG. 1 comprises:
a sinusoidal signal generator 1;
a power amplifier 2;
two identical impedances 3 and 4;
a differential amplifier 5;
a first synchronous detector comprising an analog multiplier 6 and a low-pass filter 8;
a second synchronous detector comprising an analog multiplier 7 and a low-pass filter 9;
two identical coils 14 and 15 constituting a probe 18 remote from the remainder of the test device and connected to the latter by two coaxial cables 12 and 13.

The probe 18 is placed on the surface of a metal part 17 to be tested. The probe 18 is usually moved at constant speed over the surface to scan all of the surface. The coils 14 and 15 are coupled electromagnetically to the part 17 and are coupled to each other because of their close proximity. The coils 14 and 15 carry two sinusoidal alternating currents in the same direction. In the example shown in FIG. 1 the two coils 14, 15 are wound in the same direction and the magnetic fluxes of the two coils are added together.

If a defect 16 is aligned with the coil 14, for example, the eddy currents generated by the coil 14 have a different configuration than those generated by the coil 15. This causes a difference between the complex impedances of the coils 14 and 15. In some cases it is beneficial to reverse the flux in one of the coils to increase the resolution.

Figure 2:
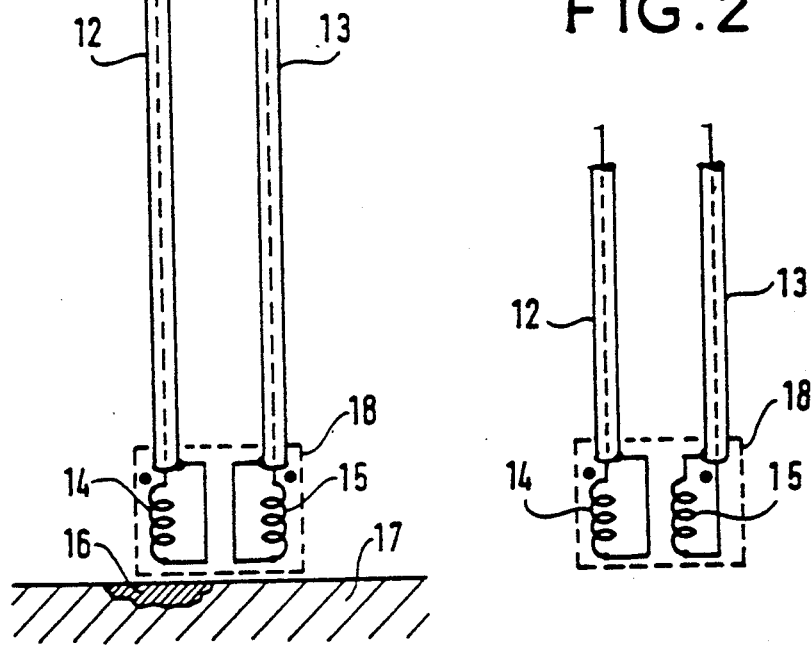
FIG. 2 shows the probe of this prior art device after interchanging the conductors connected to one of the coils to apply additive flux/subtractive flux switching by the prior art method.

FIG. 2 shows the same probe 18 in which the ends of the two conductors of the coaxial cable 13 have been interchanged at the terminals of the coil 15 so that the fluxes generated by the coils 14 and 15 are subtracted rather than added.

An input of the power amplifier 2 is connected to an output terminal 22 of the generator 1 which supplies a sinusoidal excitation signal. An output of the differential amplifier 5 is connected to a first input of the multiplier 6 and to a first input of the multiplier 7. A second input of the multiplier 6 is connected to an output terminal 21 of the generator 1 which supplies a first sinusoidal reference signal at the same frequency as the signal at the excitation output terminal 22. The second input of the multiplier 7 is connected to an output terminal 23 of the generator 1 which supplies a second sinusoidal reference signal 90° out of phase to the first reference signal.

The outputs of the multipliers 6 and 7 are respectively connected to the inputs of a low-pass filter 8 and a low-pass filter 9. The outputs of the filters 8 and 9 are connected to two output terminals respectively supplying signals respectively representing the real part and the imaginary part of the difference between the complex impedances of the coils 14 and 15. These signals can be recorded by a graphic recorder or processed by a digital computer, for example.

The excitation current to each of the coils 14 and 15 is obtained from the output of the power amplifier 2 through the impedances 3 and 4 which form with the coils 14 and 15 a Wheatstone bridge. A first end of the impedance 3 and a first end of the impedance 4 are connected to the output of the power amplifier 2. A first end of the coil 14 is connected to a reference potential of the test device by the shield of the cable 12. A first end of the coil 15 is connected to the reference voltage of the test device by the shield of the cable 13. A second end of the coil 14 is connected to a second end of the impedance 3 by the central conductor of the cable 12. A second end of the coil 15 is connected to a second end of the impedance 4 by the central conductor of the cable 13. The second ends of the impedances 3 and 4 constitute the outputs of the Wheatstone bridge and are respectively connected to an inverting input and to a non-inverting input of the differential amplifier 5. Calculation shows that for a sinusoidal signal the output voltage of the bridge is a function of the complex impedances 14 and 15. Each of the impedances 3 and 4 is made up of a pure resistance in parallel with an inductance, the values of which are chosen to maximize the sensitivity of the Wheatstone bridge.

Figure 3:
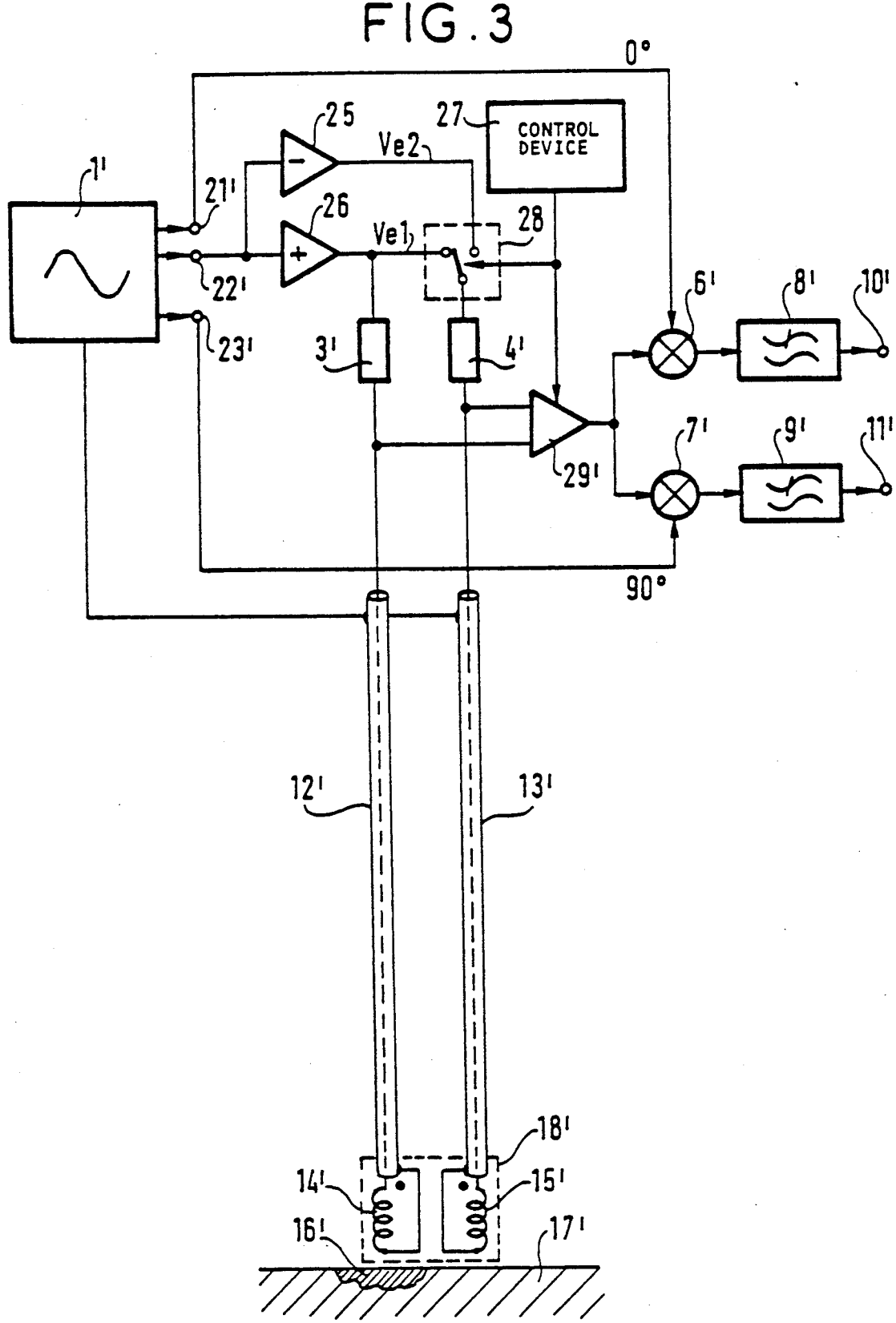
FIG. 3 is a block diagram of one embodiment of a device in accordance with the invention.

FIG. 3 is a block diagram of one embodiment of a device in accordance with the invention, parts analogous to those of the prior art device having the same reference number "primed".

This embodiment comprises:
a generator 1';
two identical impedances 3' and 4';
two identical coils 14' and 15' constituting a probe 18' and connected to the remainder of the test device by two coaxial cables 12' and 13';
two power amplifiers 25 and 26;
a control device 27 in the form, for example, of a manual switch providing a binary control signal for additive flux/subtractive flux switching;
a changeover relay 28;
an amplifier 29' having two signal inputs and a control input adapted to add or subtract the voltages applied to said two signal inputs according to the value of a binary control signal applied to the control input;
a synchronous detector comprising an analog multiplier 6' and a low-pass filter 8';
a synchronous detector comprising an analog multiplier 7' and a low-pass filter 9'.

Compared with the prior art device, the power amplifier 2 is replaced by two power amplifiers 25, 26 whose gains −A, +A have the same absolute value A but are of opposite sign and whose inputs are both connected to the output terminal 22' of the generator 1' which supplies a sinusoidal excitation signal.

The differential amplifier 5 is replaced by the amplifier 29'. Its two signal inputs are respectively connected to the two outputs of a Wheatstone bridge made up of the two impedances 3' and 4' and the two coils 14' and 15'. The output of the amplifier 29 is connected to first inputs of the two multipliers 6' and 7'. Second inputs of the multipliers 6' and 7' are respectively connected to output terminals 21' and 23' of the generator 1' which supplies them with two sinusoidal reference signals 90° out of phase. The outputs of the multipliers 6' and 7' are respectively connected to the inputs of the two low-pass filters 8' and 9'. The outputs of the latter are respectively connected to the two outputs terminals 10' and 11' of the test device respectively supplying two signals respectively representing the real part and the imaginary part of the difference between the impedances of the coils 14' and 15'.

The changeover relay 28 has two signal inputs, a signal output and a control input. It connects its output to one of its two inputs. The two inputs of the relay 28 are respectively connected to the outputs of the amplifiers 25 and 26. The output of the relay 28 is connected to a first end of the impedance 4'. The output of the amplifier 25 is further connected to a first end of the impedance 3'. The control inputs of the relay 25 and the amplifier 29' receive the binary signals supplied by the control device 27.

A first end of the coil 14' is connected to a reference voltage of the test device by the shield of the cable 12'. A first end of the coil 15' is connected to the reference voltage of the test device by the shield of the cable 13'. A second end of the coil 14' is connected to a second end of the impedance 3' by the central conductor of the cable 12'. A second end of the coil 15' is connected to a second end of the impedance 4' by the central conductor of the cable 13'. The second ends of the impedances 3' and 4' constitute the outputs of the Wheatstone bridge and are respectively connected to the two signal inputs of the amplifier 29'.

For one value of the binary control signal the relay 28 is in a first position connecting the first end of the impedance 4' to the output of the amplifier 26. The impedances 3' and 4' then receive the same excitation signal Ve1. The coils 14' and 15' then generate magnetic fluxes with the same orientation and which are added together. For this value of the control signal the amplifier 29' operates as a differential amplifier. The test device as a whole operates in exactly the same way as the prior art device described previously with reference to FIG. 1.

For the opposite value of the control signal the relay 28 connects the first end of the impedance 4' to the output of the amplifier 25. The impedances 3' and 4' then receive two different excitation signals Ve1 and Ve2 of the same magnitude but of opposite sign. The coils 14' and 15' then carry two currents in opposite directions which generate two magnetic fluxes which are subtracted. For this value of the control signal the amplifier 29' adds the input two voltages and amplifies their sum. This change in comparison with the previous situation compensates for the fact that the direction of the current has been reversed in the impedance 4' and the coil 15'. The synchronous detectors 6', 8' and 7', 9' operate in a similar way to the synchronous detectors of a prior art test device.

The man skilled in the art will know how to make an amplifier 29' subtract or add according to a binary control signal. For example, an operational amplifier, an electromechanical or semiconductor switch and a few resistors may be used.

The scope of the invention is not limited to the embodiment described above. The man skilled in the art will know other ways to provide two excitation signals in phase opposition, using a centre-tapped transformer, for example. The generators 1 and 1' supply a sinusoidal signal but the scope of the invention is not limited to this type of excitation signal. There are numerous ways to implement the amplifier 29'. For example, it may comprise a summing amplifier connected in parallel with a subtracting amplifier having the same gain, their outputs being switched by a switch to select the signal supplied by one of the two amplifiers.

There is claimed:

1. A non-destructive eddy current test device using additive flux/substractive flux switching, comprising:
   a control means for selecting either additive flux or subtractive flux operation;
   supplying means for supplying first and second excitation signals alternating at the same frequency but in phase opposition to one another;
   two analogous coils adjacent one another and electromagnetically coupled to a part under test so as to create two fluxes therein when excitation signals are supplied to said coils;
   feeding means controlled by said control means and connected to said supplying means and to said coils for feeding said excitation signals to said coils whereby each coil will have a terminal voltage corresponding to an impedance of the respective coil, said feeding means feeding said first excitation signal to said first coil and feeding either of said first or second excitation signals to said first coil in accordance with the selection by said control means; and
   measuring means connected to said coils for measuring the difference between the impedances of said first and second coils, by either adding or subtracting the terminal voltages of said first and second coils in accordance with the selection by said control means.

2. A device according to claim 1 wherein said supplying means comprises two power amplifiers of equal and opposite gain and whose inputs are adapted to receive the same signal.

3. A device according to claim 1 wherein said measuring means comprises a two-input amplifier adapted to add or subtract two voltages applied to said inputs, according to the value of a binary control signal.

* * * * *